(12) United States Patent
Matsubara et al.

(10) Patent No.: US 10,704,024 B2
(45) Date of Patent: Jul. 7, 2020

(54) METHOD FOR PRODUCING MESENCHYMAL CELLS WITH PROMOTED C-MPL RECEPTOR EXPRESSION ON CELL SURFACE

(71) Applicant: AdipoSeeds, Inc., Tokyo (JP)

(72) Inventors: Yumiko Matsubara, Tokyo (JP); Yasuo Ikeda, Tokyo (JP); Yukako Uruga, Tokyo (JP)

(73) Assignee: Adiposeeds, Inc., Tokyo (JP)

( * ) Notice: Subject to any disclaimer, the term of this patent is extended or adjusted under 35 U.S.C. 154(b) by 67 days.

(21) Appl. No.: 15/753,028

(22) PCT Filed: Aug. 5, 2016

(86) PCT No.: PCT/JP2016/003626
§ 371 (c)(1),
(2) Date: Feb. 15, 2018

(87) PCT Pub. No.: WO2017/033415
PCT Pub. Date: Mar. 2, 2017

(65) Prior Publication Data
US 2018/0245046 A1 Aug. 30, 2018

(30) Foreign Application Priority Data

Aug. 21, 2015 (JP) .................. 2015-163673

(51) Int. Cl.
*C12N 5/077* (2010.01)
*A61P 7/04* (2006.01)
*A61K 38/00* (2006.01)
*A61K 31/4152* (2006.01)

(52) U.S. Cl.
CPC ........ *C12N 5/0653* (2013.01); *A61K 31/4152* (2013.01); *A61K 38/00* (2013.01); *A61P 7/04* (2018.01); *C12N 2501/145* (2013.01)

(58) Field of Classification Search
CPC ... C12N 5/0653; C12N 2501/145; A61P 7/04; A61K 31/4152; A61K 38/00
See application file for complete search history.

(56) References Cited

U.S. PATENT DOCUMENTS 7,972,767 B2 * 7/2011 Lin .................. A61L 27/3834
435/1.1
2004/0235160 A1 * 11/2004 Nishikawa .......... C12N 5/0647
435/370

FOREIGN PATENT DOCUMENTS

| JP | 2013-521806 | 6/2013 |
| WO | WO 2010/045310 | 4/2010 |
| WO | 2011/116117 | 9/2011 |
| WO | 2013/175759 | 11/2013 |
| WO | 2014/208100 | 12/2014 |

OTHER PUBLICATIONS

Kuter et al., "Recombinant Human Thrombopoietin: Basic Biology and Evaluation of Clinical Studies." Blood, Nov. 15, 2002, vol. 100, No. 10, pp. 3457-3469.
Matsubara et al., "Culture of Megakaryocytes and Platelets from Subcutaneous Adipose Tissue and a Preadipocyte Cell Line." Methods of Mol. Biol., 2012, 788, pp. 249-258.
Matsubara et al., "Generation of Megakaryocytes and Platelets from Human Subcutaneous Adipose Tissues." Biochem Biophys. Res. Commun., Jan. 23, 2009, 378(4), pp. 716-720.
Matsubara et al., "Generation of Megakaryocytes and Platelets from Preadipocyte Cell Line 3T3-L1, But Not the Parent Cell Line 3T3, In Vitro." Biochem Biophys Res. Comm., Nov. 26, 2010, 402(4), pp. 796-800.
Matsubara et al., "OP9 Bone Marrow Stroma Cells Differentiate into Megakaryocytes and Platelets." PLoS One, Mar. 2013, vol. 8, Issue 3, 9 pages.
Murone et al., "Hematopoietic Deficiencies in c-mpl and TPO Knockout Mice." Stem Cells, 1998, 16, 6 pages.
Nakamura et al., "Expandable Megakaryocyte Cell Lines Enable Clinically Applicable Generation of Platelets from Human Induced Pluripotent Stem Cells." Cell Stem Cell 14, Apr. 3, 2014, pp. 535-548.
Notification of Transmittal of Copies of Translation of the International Preliminary Report on Patentability, and International Preliminary Report on Patentability, for International Application No. PCT/JP2016/003626 dated Mar. 8, 2018 issued by the International Bureau of WIPO, 6 pages.
Ono et al. "Induction of Functional Platelets from Mouse and Human Fibroblasts by p45NF-E2/Maf." Blood, Nov. 1, 2012, vol. 120, No. 19, pp. 3812-3821, 11 pages.
Reems et al., "In Vitro Megakaryocyte Production and Platelet Biogenesis: State of the Art." Transfus Med Rev., Jan. 2010, 24(1): pp. 33-43, 16 pages.

(Continued)

*Primary Examiner* — Taeyoon Kim
(74) *Attorney, Agent, or Firm* — Occhiuti & Rohlicek LLP (57) ABSTRACT

An object of the present invention is to provide a method of simply and efficiently promoting expression of c-MPL on a surface of a mesenchymal cell. The present invention provides a method for producing a mesenchymal cell with promoted expression of a c-MPL receptor on the cell surface, comprising Step A of culturing the mesenchymal cell in a mesenchymal cell culturing basic medium comprising a c-MPL receptor active substance; and Step B of obtaining the mesenchymal cell with promoted expression of a c-MPL receptor on the cell surface.

6 Claims, 1 Drawing Sheet
Specification includes a Sequence Listing.

(56) References Cited

OTHER PUBLICATIONS

Sato et al., "Binding and Regulation of Thrombopoietin to Human Megakaryocytes." British Journal of Haematology, 1998, 100, pp. 704-711.
Sunohara et al., "GATA-dependent Regulation of TPO-induced c-mpl Gene Expression During Megakaryopoiesis." Okajimas Folia Anat. Jpn., 90(4), pp. 101-106, Feb. 2014.
Takayama, et al., "Generation of Functional Platelets from Human Embryonic Stem Cells in Vitro Via ES-sacs, VEGF-promoted Structures that Concentrate Hematopoietic Progenitors." Blood, Jun. 1, 2008, vol. 111, No. 11, pp. 5298-5306, 10 pages.

\* cited by examiner

Human preadipocytes: immunostaining of MPL (+DAPI)

Cultured without TPO​ ​ ​ ​ ​ ​ ​ ​ ​ Cultured with TPO

SEQUENCE LISTING

```
<160> NUMBER OF SEQ ID NOS: 4

<210> SEQ ID NO 1
<211> LENGTH: 353
<212> TYPE: PRT
<213> ORGANISM: Homo sapiens
<220> FEATURE:
<221> NAME/KEY: misc_feature
<223> OTHER INFORMATION: Inventor:MATSUBARA, Yumiko; IKEDA, Yasuo;
      URUGA, Yukako

<400> SEQUENCE: 1

Met Glu Leu Thr Glu Leu Leu Leu Val Val Met Leu Leu Leu Thr Ala
1               5                   10                  15

Arg Leu Thr Leu Ser Ser Pro Ala Pro Pro Ala Cys Asp Leu Arg Val
                20                  25                  30

Leu Ser Lys Leu Leu Arg Asp Ser His Val Leu His Ser Arg Leu Ser
            35                  40                  45

Gln Cys Pro Glu Val His Pro Leu Pro Thr Pro Val Leu Leu Pro Ala
        50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
            180                 185                 190
```

Asn Glu Leu Pro Asn Arg Thr Ser Gly Leu Leu Glu Thr Asn Phe Thr
        195                 200                 205

Ala Ser Ala Arg Thr Thr Gly Ser Gly Leu Leu Lys Trp Gln Gln Gly
    210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
                260                 265                 270

Asp Ile Ser Ser Gly Thr Ser Asp Thr Gly Ser Leu Pro Pro Asn Leu
            275                 280                 285

Gln Pro Gly Tyr Ser Pro Ser Pro Thr His Pro Thr Gly Gln Tyr
        290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
                340                 345                 350

Gly

<210> SEQ ID NO 2
<211> LENGTH: 1062
<212> TYPE: DNA
<213> ORGANISM: Homo sapiens

<400> SEQUENCE: 2

```
atggagctga ctgaattgct cctcgtggtc atgcttctcc taactgcaag gctaacgctg      60
tccagcccgg ctcctcctgc ttgtgacctc cgagtcctca gtaaactgct tcgtgactcc     120
catgtccttc acagcagact gagccagtgc ccagaggttc acccttttgcc tacacctgtc     180
ctgctgcctg ctgtggactt tagcttggga gaatggaaaa cccagatgga ggagaccaag     240
gcacaggaca ttctgggagc agtgaccctt ctgctggagg gagtgatggc agcacgggga     300
caactgggac ccacttgcct ctcatccctc ctggggcagc tttctggaca ggtccgtctc     360
ctccttgggg ccctgcagag cctccttgga acccagcttc ctccacaggg caggaccaca     420
gctcacaagg atcccaatgc catcttcctg agcttccaac acctgctccg aggaaaggtg     480
cgtttcctga tgcttgtagg agggtccacc ctctgcgtca ggcgggcccc acccaccaca     540
gctgtcccca gcagaaccct ctctagtcct cacactgaac gagctcccaa caggacttct     600
ggattgttgg agacaaactt cactgcctca gccagaacta ctggctctgg gcttctgaag     660
tggcagcagg gattcagagc caagattcct ggtctgctga ccaaacctc aggtccctg     720
gaccaaatcc ccggatacct gaacaggata acgaactct tgaatggaac tcgtggactc     780
tttcctggac cctcacgcag gaccctagga gccccggaca tttcctcagg aacatcagac     840
acaggctccc tgccacccaa cctccagcct ggatattctc cttccccaac ccatcctcct     900
actggacagt atacgctctt ccctcttcca cccaccttgc ccaccctgt ggtccagctc     960
caccccctgc ttcctgaccc ttctgctcca acgcccaccc ctaccagccc tcttctaaac    1020
acatcctaca cccactccca gaatctgtct caggaagggt aa                       1062
```

<210> SEQ ID NO 3

```
<211> LENGTH: 163
<212> TYPE: PRT
<213> ORGANISM: Homo sapiens

<400> SEQUENCE: 3

Met Glu Leu Thr Glu Leu Leu Val Val Met Leu Leu Thr Ala
1               5                   10                  15

Arg Leu Thr Leu Ser Ser Pro Ala Pro Ala Cys Asp Leu Arg Val
                20              25              30

Leu Ser Lys Leu Leu Arg Asp Ser His Val Leu His Ser Arg Leu Ser
            35              40              45

Gln Cys Pro Glu Val His Pro Leu Pro Thr Pro Val Leu Leu Pro Ala
50              55                      60

Val Asp Phe Ser Leu Gly Glu Trp Lys Thr Gln Met Glu Glu Thr Lys
65                  70              75                  80

Ala Gln Asp Ile Leu Gly Ala Val Thr Leu Leu Leu Glu Gly Val Met
                85              90                  95

Ala Ala Arg Gly Gln Leu Gly Pro Thr Cys Leu Ser Ser Leu Leu Gly
            100             105                 110

Gln Leu Ser Gly Gln Val Arg Leu Leu Leu Gly Ala Leu Gln Ser Leu
            115             120                 125

Leu Gly Thr Gln Leu Pro Pro Gln Gly Arg Thr Thr Ala His Lys Asp
    130             135                 140

Pro Asn Ala Ile Phe Leu Ser Phe Gln His Leu Leu Arg Gly Lys Val
145                 150                 155                 160

Arg Phe Leu

<210> SEQ ID NO 4
<211> LENGTH: 489
<212> TYPE: DNA
<213> ORGANISM: Homo sapiens

<400> SEQUENCE: 4
atggagctga ctgaattgct cctcgtggtc atgcttctcc taactgcaag gctaacgctg      60
tccagcccgg ctcctcctgc ttgtgacctc cgagtcctca gtaaactgct tcgtgactcc     120
catgtccttc acagcagact gagccagtgc ccagaggttc accctttgcc tacacctgtc     180
ctgctgcctg ctgtggactt tagcttggga gaatggaaaa cccagatgga ggagaccaag     240
gcacaggaca ttctgggagc agtgaccctt ctgctggagg gagtgatggc agcacgggga     300
caactgggac ccacttgcct ctcatccctc ctggggcagc tttctggaca ggtccgtctc     360
ctccttgggg ccctgcagag cctccttgga acccagcttc ctccacaggg caggaccaca     420
gctcacaagg atcccaatgc catcttcctg agcttccaac acctgctccg aggaaaggtg     480
cgtttcctg                                                             489
```

METHOD FOR PRODUCING MESENCHYMAL CELLS WITH PROMOTED C-MPL RECEPTOR EXPRESSION ON CELL SURFACE

CROSS REFERENCE TO RELATED APPLICATIONS

This application is a National Phase under 35 USC 371 of International Application No. PCT/JP2016/003626 filed on Aug. 5, 2016, which claims priority to Japanese Application No. 2015-163673 filed Aug. 21, 2015, the contents of which are hereby incorporated by reference in their entirety.

TECHNICAL FIELD

The present invention relates to an agent for promoting expression of a c-MPL receptor on the surface of a mesenchymal cell; a method for producing a mesenchymal cell with promoted expression of a c-MPL receptor on the cell surface; and a method for promoting expression of a c-MPL receptor on the surface of a mesenchymal cell.

BACKGROUND ART

Platelet transfusion is only one therapy against thrombocytopenia caused by e.g., bleeding associated with accidents and during use of anti-cancer agents. Platelet preparations to be used for the time are produced completely (100%) depending upon blood donation with good intentions, at present. Platelets are very fragile and a method enabling platelets for use in therapy to store for a long time has not yet been developed. Actually, it is reported that the storage life of platelets in the latest medical institutions is four days; however, in consideration of time required for inspection and shipment, substantial storage life thereof in clinical sites including clinics is conceivably about three days. Likewise, many blood banks have a difficulty in storing platelets while keeping freshness at all times. In addition, the supply amount of platelet preparations is likely to vary dependent upon a decrease of blood donors and an increase of blood donors affected with viral infectious diseases.

In the circumstances, recently, a novel platelet supply source has attracted attention, which has been developed in place of blood donation having such problems (non-patent document 1). As an example, development of a technique of producing a large amount of platelets in vitro using somatic stem cells, i.e., hematopoietic stem cells (umbilical cord blood stem cells) is known. However, this technique has not yet been put into practical use, because an in vitro method for proliferating hematopoietic stem cells per se has not yet been established. In contrast, pluripotent stem cells, i.e., embryonic stem (ES) cells have an advantage in that they can be unlimitedly proliferated in vitro and have attracted attention as a supply source for producing blood cells including platelets. In this respect, techniques for producing mature megakaryocytes and platelets from human ES cells have been already reported (non-patent document 2). However, in the techniques (methods), the production efficiency of platelets is low and tens of thousands of petri dishes are required for producing a single blood transfusion preparation. These methods were insufficient from a practical point of view.

In transfusion of platelets, refractory to platelet transfusion is raised as a problem. At the first-time transfusion, platelets having a different human leukocyte antigen (HLA) from a patient can be used; however, a specific antibody against the HLA is produced in the patient's body when transfusion is repeated, with the result that the platelets are rejected immediately upon transfusion. In addition, since platelets have own blood type, i.e., an allogeneic human platelet antigen (HPA), refractory to transfusion caused by incompatibility of HPA types is also known. As a technique which can overcome this problem, techniques for producing megakaryocytes and platelets from human induced pluripotent stem (iPS) cells have been reported (non-patent document 3). For example, if platelets are induced from a patient-derived iPS cells, it is theoretically possible to produce a rejection-free custom-made platelet preparation. However, in producing platelets from iPS cells, at least about 50 days are required for producing platelets from fibroblasts (non-patent document 3). For the reason, this production method was insufficient from a practical point of view. In the meantime, as a method for producing platelets from fibroblasts, a technique called direct reprogramming is known (non-patent document 4). According to this technique, the period required for producing platelets will be greatly shorter than the method for producing platelets via iPS cells. Advantageously, platelets are produced in about 14 days. However, the direct reprogramming using fibroblasts requires gene introduction. The effect of the presence of a gene transfer vector on safety is concerned.

As a culture solution for inducing differentiation of hematopoietic stem cells into megakaryocytes, platelets, MKLI medium (megakaryocyte lineage induction medium) is known. The MKLI medium is a medium prepared by adding, 2 mM L-glutamine, a 100 U/mL penicillin-streptomycin solution, 0.5% bovine serum albumin, 4 µg/mL LDL cholesterol, 200 µg/mL iron-saturated transferrin (iron-bound transferrin), 10 µg/mL insulin, 50 µM 2-β-mercaptoethanol, nucleotides (20 µM for each of ATP, UTP, GTP and CTP) and 50 ng/mL thrombopoietin (thrombopoietin: TPO) to Iscove's Modified Dulbecco's Medium (IMDM) (non-patent document 5). The present inventors have so far conducted studies on a technique for inducing differentiation of cells excluding hematopoietic stem cells into megakaryocytes, platelets. As a result, they have found that if preadipocytes derived from a human subcutaneous adipose tissue (non-patent documents 5, 6) and mouse-derived preadipocytes (non-patent documents 5, 7) are cultured in the MKLI medium, they can be differentiated into megakaryocytes, platelets. The present inventors further conducted studies and have found a further excellent method for successfully producing megakaryocytes and/or platelets (Patent Document 1). The production method of Patent Document 1 is a production method comprising culturing mesenchymal cells in a mesenchymal cell culturing basic medium comprising an iron ion and an iron transporter, and collecting megakaryocytes and/or platelets from a culture. In the production method of Patent Document 1, it is possible to produce megakaryocytes having the ability to make platelets and/or platelets having thrombus forming ability from mesenchymal cells such as preadipocytes in a relatively short period of time, simply and in a large amount as well as at lower cost or more efficiently in vitro even if e.g., TPO is not added to the medium.

As described above, the production method of Patent Document 1 is an excellent production method, which overcame drawbacks of conventional production methods for platelets using hematopoietic stem cells, ES cells or iPS cells. However, as the results of analysis (made by the present inventors) for the relationship between the type of surface antigen of mesenchymal cells, such as preadipocytes (before differentiation induction into megakaryocytes or platelets) and the differentiation efficiency of the mesenchymal cells into e.g., megakaryocytes in differentiation induction into e.g., megakaryocytes, it was shown that c-MPL receptor-positive mesenchymal cells are differentiated into megakaryocytes or platelets with extremely high efficiency, compared to c-MPL receptor-negative mesenchymal cells. However, the ratio of c-MPL receptor positive cells in mesenchymal cells such as preadipocytes was extremely low: about 0.5 to 1%.

A c-MPL receptor is known as an in vivo TPO receptor. More specifically, TPO is known as a ligand of a c-MPL receptor in vivo. c-MPL is a glycoprotein, which expresses on hematopoietic stem cells and megakaryocyte lineage cells and belongs to a cytokine receptor gene family. It has been suggested c-MPL is deeply involved in platelet production as a receptor for a novel factor involved in platelet production. TPO is synthesized in the liver as a proprotein consisting of 353 amino acids and becomes a mature protein molecule by cleaving a signal peptide of 21 amino acids. The mature protein molecule consists of two domains having a high homology with erythropoietin and a highly glycosylated carboxy terminal important for protein stability (non-patent document 8). It is reported that, in a TPO gene or c-MPL receptor gene-defective mouse, the number of platelets decreases down to about 10 to 20% of that of a wild type mouse (Non-Patent Document 9). From this, it is suggested that TPO and a c-MPL receptor are involved in regulation of the pathway for producing platelets from hematopoietic stem cells.

In Non-Patent Document 10, it is described that the activity of the promotor of a c-MPL receptor gene in human megakaryoblastic leukemia cell line, i e., CMK cells, is induced by TPO. In Non-Patent Document 10, the activity of the promotor of a c-MPL receptor gene is measured based on the luciferase activity by the expression of a luciferase gene ligated to a portion downstream of the promoter. However, in Non-Patent Document 10, it is not to say that the effect of TPO on expression of a c-MPL receptor on a cell surface is confirmed. In contrast, Non-Patent Document 11 shows that TPO reduces expression of a c-MPL receptor on the surface of CMK cells.

PRIOR ART DOCUMENTS

Patent Document

Patent Document 1: International Publication No. WO 2014/208100.

Non-Patent Documents

Non-patent document 1: Reems J A, Pineault N, Sun S. In vitro megakaryocyte production and platelet biogenesis: state of the art. Transfus Med Rev. 2010; 24 (1): 33-43.
Non-patent document 2: Takayama N, Nishikii H, Usui J, et al. Generation of functional platelets from human embryonic stem cells in vitro via ES-sacs, VEGF-promoted structures that concentrate hematopoietic progenitors. Blood. 2008; 111 (11): 5298-5306.
Non-patent document 3: Nakamura S, Takayama N, Hirata S, et al. Expandable Megakaryocyte Cell Lines Enable Clinically Applicable Generation of Platelets from HumanInduced Pluripotent Stem Cells. Cell Stem Cell. 2014 Feb. 12.pii: S1934-5909 (14)00012-5. doi: 10.1016/j.stem.2014.01.011.
Non-patent document 4: Ono Y, Wang Y, Suzuki H, et al. Induction of functional platelets from mouse and human fibroblasts by p45NF-E2/Maf. Blood. 2012; 120: 3812-3821.
Non-patent document 5: Matsubara Y, Murata M, Ikeda Y, Culture of megakaryocytes and platelets from subcutaneous adipose tissue and a preadipocyte cell line. MethodsMol Biol. 2012; 788: 249-258.
Non-patent document 6: Matsubara Y, Saito E, Suzuki H, Watanabe N, Murata M, et al. Generation of megakaryocytes/platelets from human subcutaneous adipose tissues. Biochem Biophys Res Commun. 2009; 378: 716-720.
Non-patent document 7: Matsubara Y, Suzuki H, Ikeda Y, Murata M. Generation of megakaryocytes/platelets from preadipocyte cell line 3T3-L1, but not the parent cell line 3T3, in vitro. Biochem Biophys Res Commun. 2010; 402: 796-800.
Non-patent document 8: Kuter D J, and Begley C G. Recombinant human thrombopoietin: basic biology and evaluation of clinical studies. Blood 2002; 100:3457-3469.
Non-patent document 9: Murone M1, Carpenter D A, de Sauvage F J. Hematopoietic deficiencies in c-mpl and TPO knockout mice. Stem Cells 1998; 16(1): 1-6.
Non-patent document 10: Sunohara M, Morikawa S, Fuse A, Sato I. GATA-dependent regulation of TPO-induced c-mpl gene expression during megakaryopoiesis. Okajimas Folia Anat Jpn. 2014; 90(4): 101-6.
Non-patent document 11: Sato T, Fuse A, Niimi H, Fielder P J, Avraham H. Binding and regulation of thrombopoietin to human megakaryocytes. Br J Haematol. 1998 March; 100(4): 704-11.

SUMMARY OF THE INVENTION

Object to be Solved by the Invention

An object of the present invention is to provide a method for simply and efficiently promoting expression of c-MPL on the surface of a mesenchymal cell.

Means to Solve the Object

The present inventors conducted intensive studies to attain the object. They have found that when a mesenchymal cell such as a preadipocytes is subjected to maintenance culture performed in a basic medium, expression of a c-MPL receptor on the surface of a mesenchymal cell is promoted by adding TPO to the basic medium, and have achieved the present invention. Considering the disclosure in Non-Patent Document 11 that TPO reduces expression of a c-MPL receptor on the surface of CMK cells, the finding by the present inventors is a surprise.

More specifically, the present invention relates to (1) an agent for promoting expression of a c-MPL receptor on the surface of a mesenchymal cell, comprising a c-MPL receptor active substance;

(2) the agent for promoting expression of a c-MPL receptor on a surface of a mesenchymal cell according to (1), wherein the c-MPL receptor active substance is one or more substances selected from the group consisting of TPO or a derivative thereof, Romiplostim and Eltrombopag olamine; and (3) The agent for promoting expression of a c-MPL receptor on a surface of a mesenchymal cell according to (1) or (2), wherein the mesenchymal cell is a preadipocyte.

The present invention also relates to (4) a method for producing a mesenchymal cell with promoted expression of a c-MPL receptor on a cell surface, comprising Step A of culturing the mesenchymal cell in a mesenchymal cell culturing-basic medium comprising a c-MPL receptor active substance; and, Step B of obtaining the mesenchymal cell with promoted expression of a c-MPL receptor on the cell surface;

(5) The method for producing a mesenchymal cell with promoted expression of a c-MPL receptor on a cell surface according to (4), wherein the c-MPL receptor active substance is one or more substances selected from the group consisting of TPO or a derivative thereof, Romiplostim and Eltrombopag olamine;

(6) The method for producing a mesenchymal cell with promoted expression of a c-MPL receptor on a cell surface according to (4) or (5), wherein the mesenchymal cell is a preadipocyte;

(7) The method for producing a mesenchymal cell with promoted expression of a c-MPL receptor on a cell surface according to any one of (4) to (6), wherein the mesenchymal cell culturing-basic medium further comprises serum; and (8) The method for producing a mesenchymal cell with promoted expression of a c-MPL receptor on a cell surface according to any one of (4) to (7), wherein a ratio of the c-MPL receptor-positive mesenchymal cells in the mesenchymal cell population obtained in Step B is 1% or more.

The present invention further relates to (9) A method for promoting expression of a c-MPL receptor on a surface of a mesenchymal cell, comprising Step A of culturing the mesenchymal cell in a mesenchymal cell culturing basic medium comprising a c-MPL receptor active substance.

Effect of the Invention

According to the present invention, expression of c-MPL on the surface of a mesenchymal cell can be simply and efficiently promoted. More specifically, according to the present invention, a mesenchymal cell with promoted expression of a c-MPL receptor on the cell surface can be simply and efficiently produced.

Since a mesenchymal cell with promoted expression of a c-MPL receptor on the cell surface is differentiated at a high ratio at the time of differentiation induction into megakaryocytes or platelets (see, for example, Example 2 described later), the mesenchymal cell with promoted expression of a c-MPL receptor on the cell surface can be suitably used for e.g., efficiently producing megakaryocytes or platelets. In addition, the number of mesenchymal cells with promoted expression of a c-MPL receptor on the cell surface does not drastically increase during differentiation induction into megakaryocytes or platelets, the present invention, which induces differentiation of the mesenchymal cell into megakaryocytes or platelets, is extremely significant.

MODE OF CARRYING OUT THE INVENTION

<Method for Producing a Mesenchymal Cell with Promoted Expression of a c-MPL Receptor>

The method for producing a mesenchymal cell with promoted expression of a c-MPL receptor according to the present invention (hereinafter simply referred to as "the production method of the present invention") is not particularly limited as long as it is a method comprising Step A of culturing the mesenchymal cell in a mesenchymal cell culturing basic medium comprising a c-MPL receptor active substance; and, Step B of obtaining the mesenchymal cell with promoted expression of a c-MPL receptor.

The "medium" used herein is prepared by adding water to "medium components" which can be used for culturing cells. When a mesenchymal cell such as preadipocyte is cultured in a mesenchymal cell culturing basic medium comprising a c-MPL receptor active substance, expression of a c-MPL receptor on the surface of a mesenchymal cell is promoted, although details of the mechanism are not known. Note that, as the "c-MPL receptor active substance" in the production method of the present invention, an "agent for promoting expression of a c-MPL receptor on the surface of a mesenchymal cell" (described later) of the present invention may be used.

(Step A)

Step A is not particularly limited as long as it is a step of culturing a mesenchymal cell in a mesenchymal cell culturing basic medium comprising a c-MPL receptor active substance. Such a culture step is an in vitro culture step.

(Mesenchymal Cell to be Used in the Present Invention)

The mesenchymal cell to be used in the present invention is not particularly limited as long as it is a mesenchymal cell with promoted expression of a c-MPL receptor on the cell surface by culturing the mesenchymal cell in a mesenchymal cell culturing basic medium comprising a c-MPL receptor active substance. As the mesenchymal cells, (a) preadipocytes (adipose progenitor cells), (b) mesenchymal stem cells and (c) stromal cells can be mentioned. As the mesenchymal stem cells, subcutaneous adipose tissue-derived mesenchymal stem cells and bone marrow mesenchymal stem cells can be mentioned. As the stromal cells, adipose tissue-derived stromal cells, bone marrow stromal cells, prostate-derived stromal cells and endometrial-derived stromal cells can be mentioned. As the preferable mesenchymal cells, preadipocytes and subcutaneous adipose tissue-derived mesenchymal stem cells can be mentioned. The mesenchymal cells to be used in the invention can be a cell line or cells (including primary cultured cells and subcultured cells) taken from a tissue. As specific examples of the mesenchymal cells to be used in the invention, human primary-culture preadipocytes (HPAd cell), mouse primary-culture progenitor cells (subcutaneous adipose tissue-derived), established mouse stromal cells (OP9 cells), established mouse bone marrow mesenchymal stem cells (HS-22 cells) and established mouse preadipocytes (3T3-L1 cells) can be mentioned.

As the cell line of the mesenchymal cells and a mesenchymal cell taken from a tissue, a cell commercially available from companies such as Lonza, PromoCell, CELL APPLICATIONS and the JCRB cell bank of the National Institute of Biomedical Innovation (the name has been changed to National Institute of Biomedical Innovation, Health and Nutrition) can be used; however, the mesenchymal cell taken from a tissue of a subject, to which megakaryocytes or platelets obtained by differentiation induction from the "mesenchymal cell with promoted expression of a c-MPL receptor on the cell surface" obtained by the production method of the present invention, is preferably mentioned to be administered and used, because if such mesenchymal cells are used, the HLA type and HPA type of the megakaryocytes or platelets coincide with those of the subject to be administered, with the result that, when the megakaryocytes or platelets are administered to the subject, endogenous antibodies that cross-react with the megakaryocytes or platelets are not induced and a refractory state is not resulted even if transfusion is frequently repeated.

In the case where a cell line is used as mesenchymal cells, mesenchymal cells can be prepared and established, and then put in use. The method for establishing mesenchymal cells is not particularly limited and e.g., a known method can be used. As a preferable method for establishing a preadipocyte, a method as described in Patent Document 1 (Example 15) in the background art can be mentioned, in which a preadipocytes is induced to differentiate into mature adipocytes, which are subjected to a ceiling culture known as a method for establishing mature adipocytes to obtain established preadipocytes. If the mesenchymal cell is established, differentiation potency and proliferation potency are semi-permanently maintained. Thus, if the mesenchymal cell line is e.g., cryopreserved, a "mesenchymal cell with promoted expression of a c-MPL receptor on the cell surface" can be immediately produced. As a result, production of megakaryocytes or platelets can be advantageously started by using the mesenchymal cell immediately at the time of need.

When a "mesenchymal cell with promoted expression of a c-MPL receptor on the cell surface" is used in producing megakaryocytes or platelets, in order to more efficiently produce megakaryocytes or platelets, the "mesenchymal cell (preferably preadipocyte)" to be used in the present invention is preferably, CD31 negative and CD71 positive, and more preferably, CD31 negative and CD71 positive and c-MPL receptor positive. Also, the "mesenchymal cell with promoted expression of a c-MPL receptor on the cell surface (preferably preadipocyte)" is preferably CD31 negative and CD71 positive. Note that, CD31 is known as a marker for vascular endothelial cells; whereas CD71 is known as a transferrin receptor. Patent Document 1 describes that a mesenchymal cell is preferably CD31 negative, CD71 positive and c-MPL receptor positive, in order to more efficiently produce megakaryocytes or platelets from the mesenchymal cell. As described above, when a preadipocytes is established, a CD31 negative, CD71 positive preadipocyte and preferably a CD31 negative, CD71 positive and c-MPL receptor positive preadipocyte may be previously selected from a preadipocyte and the aforementioned cell establishment method specific to the cell may be applied to them.

The preadipocytes and subcutaneous adipose tissue-derived mesenchymal stem cells can be taken from a subcutaneous adipose tissue and an adipose tissue such as a visceral tissue (fat); the bone marrow mesenchymal stem cells can be taken from a myeloid tissue; and stromal cells can be taken from e.g., an adipose tissue, a bone marrow tissue, the prostate and the endometrium. As the aforementioned preadipocytes and subcutaneous adipose tissue-derived mesenchymal stem cells, mesenchymal cells derived from an adipose tissue (preferably subcutaneous adipose tissue) can be preferably mentioned because sampling can be made by a less invasive manner and a larger number of mesenchymal cells can be more simply taken. As a method for taking mesenchymal cells from a tissue, an ordinary method can be used.

Mesenchymal cells having a predetermined cell-surface marker profile such as CD31 negative and CD71 positive mesenchymal cells, or CD31 negative, CD71 positive and c-MPL positive mesenchymal cells can be screened based on the presence or absence of their specific cell-surface markers used as indexes from a cell population including mesenchymal cells. Here, "screening of mesenchymal cells having a predetermined cell-surface marker profile" includes isolating only mesenchymal cells having a predetermined cell-surface marker profile from a cell population including mesenchymal cells such that the ratio of mesenchymal cells having a predetermined cell-surface marker profile increases from that of the cell population before screening.

A method for screening the mesenchymal cells having a predetermined cell-surface marker profile is not particularly limited. In order to more easily and quickly screen desired mesenchymal cells, for example, a method for screening mesenchymal cells having a predetermined cell-surface marker profile by using an antibody (preferably a labeled antibody, more preferably a fluorescence-labeled antibody) against each of the cell-surface markers mentioned above and based on the presence or absence of specific binding of each of the antibodies used as an index, can be suitably mentioned. The above phrase: "screened based on the presence or absence of specific binding of each of the antibodies used as an index" refers to screening cells in which the antibody against a cell-surface marker indicated as "positive" in the profile shows specific binding to the marker and screening cells in which the antibody against a cell-surface marker indicated as "negative" in the profile does not show specific binding (to the marker). To describe this more specifically, in the case where CD31 negative and CD71 positive mesenchymal cells are screened from a mesenchymal cell population, the phrase means that the cells showing no specific binding to an anti-CD31 antibody and showing specific binding to an anti-CD71 antibody are screened. The method of screening mesenchymal cells having a predetermined cell-surface marker profile based on the presence or absence of specific binding of an antibody used as an index is not particularly limited; however, a method of using e.g., a cell sorter, magnetic beads or a cell adsorption column can be mentioned. Because it is a more convenient and quick method, a method of using a cell sorter can be preferably mentioned. The method using a cell sorter is based on flow cytometry and well known to those skilled in the art. Specific methods are described in not only the instruction booklet of a cell sorter but also e.g., Japanese Unexamined Patent Application Publication (Translation of PCT Application) No. 2009-513161. The method using magnetic beads is well known to those skilled in the art as e.g., a magnetic separation method. As a specific method, a separation method by bringing magnetic beads carrying a predetermined antibody into contact with cells and collecting magnetic beads by a magnet, thereby separating cells specifically binding to the predetermined antibody can be mentioned. Furthermore, the method using a cell adsorption column is well known to those skilled in the art. As a specific method, an adsorption method by bringing cells into contact with a cell adsorption column carrying a predetermined antibody and allowing the cells except desired cells to adsorb to the column can be mentioned.

In taking CD31 negative and CD71 positive mesenchymal cells (preferably preadipocytes) and CD31 negative, CD71 positive and c-MPL positive mesenchymal cells (preferably preadipocytes) from an adipose tissue, it is preferable to use "being CD45 (marker of hematopoietic cells except erythrocytes and platelets)-negative and Ter119 (marker of erythrocytes and progenitor cells thereof)-negative" as indexes in addition to these cell-surface markers, because blood-associated cells comprised in the adipose tissue can be eliminated. Since CD45 and Ter119 are not expressed on the surface of mesenchymal cells, if cells are mesenchymal cells, it is not necessary to check whether the cells are CD45 and Ter119 negative or not. In addition, although it is not a cell-surface marker, "being 7-amino-actinomycin D (7-AAD) negative" is preferably used as an index, because dead cells comprised in the adipose tissue can be eliminated. 7-AAD intercalates in the DNA chains of dead cells and emits red fluorescence by irradiation of excitation light of 488 nm.

As a fluorescence-labeled anti-CD31 antibody, a fluorescence-labeled anti-CD71 antibody, a fluorescence-labeled anti-c-MPL antibody, a fluorescence-labeled anti-CD45 antibody and a fluorescence-labeled anti-Ter119 antibody, the fluorescence-labeled antibodies commercially available from e.g., Immuno-Biological Laboratories Co., Ltd., and BD Biosciences can be used. As 7AAD, products commercially available from e.g., BD Biosciences can be used.

In the production method of the present invention, if a mesenchymal cell which is CD31 negative and CD71 positive, preferably the mesenchymal cell further positive to c-MPL, is used, a cell population comprising mesenchymal cells having these cell surface marker profiles may be used for culture in Step A without selecting mesenchymal cells having these cell surface marker profiles; however, a cell population selected mesenchymal cells having these cell surface marker profiles is preferably used for culture in Step A. If a cell population derived from an adipose tissue is used as the cell population including mesenchymal cells, it is preferable that a cell-surface marker profile: CD45 negative and Ter119 negative is used as an index in addition to a cell-surface marker profile: CD31 negative, CD71 positive, preferably further positive to c-MPL, because blood-associated cells except mesenchymal cells can be efficiently eliminated. It is further preferable to confirm that the cells are 7-AAD negative because dead cells comprised in the adipose tissue can be efficiency eliminated.

An organism species, from which the mesenchymal cells are derived, is not particularly limited as long as it is a vertebrate. As the vertebrate, a mammal, a bird, a reptile, an amphibian and fish can be mentioned. Of them, mammals such as a human, a mouse, a rat, a guinea pig, a rabbit, a cat, a dog, a horse, a cow, a monkey, a sheep, a goat and a pig can be preferably mentioned. Of them, a human can be particularly preferably mentioned.

(c-MPL Receptor Active Substance)

The medium to be used in culture of the present invention is a medium prepared by adding a c-MPL receptor active substance to a mesenchymal cell culturing basic medium.

The c-MPL receptor active substance is not particularly limited as long as it is a substance capable of activating a c-MPL receptor, more specifically, as long as it is a substance having an activity of activating c-MPL receptor, and may be a protein or a small molecule compound having a molecular weight of 10,000 or less. Examples of such a protein may include TPO or a derivative thereof; Romiplostim; and an agonist antibody to a c-MPL receptor (Japanese unexamined Patent Application Publication No. 2009-017881). Examples of the small molecule compound having a molecular weight of 10,000 or less may include Eltrombopag olamine. TPO or a derivative thereof and Romiplostim are preferable and TPO is more preferable because the effect of promoting expression of c-MPL receptor is excellent. As Romiplostim, for example, Romiplate (registered trade mark) (manufactured by Kyowa Hakko Kirin Co., Ltd.) is mentioned. As the Eltrombopag olamine, for example Revolade (manufactured by GlaxoSmithKline K.K.) may be mentioned.

As the TPO or a derivative thereof, a protein consisting of an amino acid sequence having an identity of 80% or more, preferably 85% or more, more preferably 90% or more, further preferably 92.5% or more, more preferably 95% or more, further preferably 97% or more, more preferably 98% or more, and further preferably 99% or more with the amino acid sequence represented by SEQ ID No: 1 or 3, and having an activity of activating c-MPL receptor, is mentioned. Note that, the amino acid sequence represented by SEQ ID No: 1 is a full-length amino acid sequence of human TPO; whereas, the amino acid sequence represented by SEQ ID No: 3 is an amino acid sequence consisting of 1st to 163th amino acids and corresponding to a bioactive domain of natural human TPO. The nucleotide sequence represented by SEQ ID No: 2 is a nucleotide sequence encoding the amino acid sequence represented by SEQ ID No: 1; whereas, the nucleotide sequence represented by SEQ ID No: 4 is a nucleotide sequence encoding the amino acid sequence represented by SEQ ID No: 3.

The protein consisting of the amino acid sequence represented by SEQ ID No: 1 or 3 can be produced by any method known to those skilled in the art, such as chemical synthesis and genetic engineering technique. The protein can be prepared by, for example, integrating DNA encoding the protein consisting of the amino acid sequence represented by SEQ ID No: 1 (DNA having the nucleotide sequence represented by SEQ ID No: 2), or DNA encoding the protein consisting of the amino acid sequence represented by SEQ ID No: 3 (DNA having the nucleotide sequence represented by SEQ ID No: 4), into an appropriate expression vector; introducing the expression vector into an appropriate host cell; recovering the resultant transformant, obtaining an extract; and subjecting the extract to chromatography such as ion exchange, reversed phase and gel filtration, or affinity chromatography using a column to which an antibody against the protein consisting of the amino acid sequence represented by SEQ ID No: 1 or 3 is immobilized or these columns in combination to purify the protein.

The protein consisting of an amino acid sequence having an identity of 80% or more with the amino acid sequence represented by SEQ ID No: 1 or 3 can be produced by any method such as chemical synthesis or genetic engineering technique, known to those skilled in the art. The protein can be prepared by, for example, integrating DNA encoding a protein consisting of an amino acid sequence having an identity of 80% or more with the amino acid sequence represented by SEQ ID No: 1 or DNA encoding a protein consisting of an amino acid sequence having an identity of 80% or more with the amino acid sequence represented by SEQ ID No: 3 into an appropriate expression vector; introducing the expression vector into an appropriate host cell; recovering the resultant transformant, obtaining an extract; and subjecting the extract to chromatography such as ion exchange, reversed phase and gel filtration, or affinity chromatography having a column to which an antibody against the protein consisting of an amino acid sequence having an identity of 80% or more with the amino acid sequence represented by SEQ ID No: 1 or 3 is immobilized, or these columns in combination to purify the protein.

DNA encoding a protein consisting of an amino acid sequence having an identity of 80% or more with the amino acid sequence represented by SEQ ID No: 1 or 3 can be produced as DNA having an identity greater than or equal to a predetermined level (for example, 80% or more, preferably 85% or more, more preferably 90% or more, further preferably 92.5% or more, more preferably 95% or more, further preferably 97% or more, more preferably 98% or more, further preferably 99% or more) with the nucleotide sequence represented by SEQ ID No: 2 or 4. More specifically, to DNA consisting of the nucleotide sequence represented by SEQ ID No: 2 or 4, a mutation is introduced by a method of bringing a chemical agent into contact with the DNA, a method of applying ultraviolet rays to the DNA or a genetic engineering technique. In this manner, a DNA mutant can be obtained. One of the genetic engineering techniques, site-directed mutagenesis is useful because it is a method of successfully introducing a predetermined mutation in a predetermined position and can be carried out in accordance with a method described in e.g., Molecular Cloning, 2nd edition, Current Protocols in Molecular Biology, Supplement 1 to 38, John Wiley & Sons (1987-1997).

The c-MPL receptor active substance such as TPO or a derivative thereof, may not be chemically or biologically modified; however, the active substance may be chemically or biologically modified as long as it has an activity of activating c-MPL receptor. Examples of the modification include glycosylation of amino acids and addition of a peptide, protein and polymer to an end of the protein of the TPO or a derivative thereof. As the polymer, polyethylene glycol is mentioned. As the peptide to be added (fused) to the protein of TPO or a derivative thereof, for example, a known peptide can be used, which includes FLAG (Hopp, T. P. et al., BioTechnology (1988) 6, 1204-1210), 6×His consisting of 6 His (histidine) residues, 10×His, an influenza hemagglutinin (HA) fragment, a human c-myc fragment, a VSV-GP fragment, a p18HIV fragment, T7-tag, HSV-tag, E-tag and a SV40T antigen fragment, lck tag, an α-tubulin fragments, B-tag and Protein C fragment. Example of the other protein to be added (fused) to the protein of TPO or a derivative thereof include GST (glutathione-S-transferase), HA (influenza hemagglutinin), an immunoglobulin constant region, β-galactosidase and MBP (maltose binding protein).

Glycosylation as mentioned above can be carried out by using a glycosylation enzyme. Also, the addition (fusion) of a peptide or a protein to, e.g., an end of the protein of the TPO or a derivative thereof, can be prepared by, for example, integrating DNA encoding the protein of TPO or a derivative thereof in conjunction with DNA encoding the peptide or the protein to be added, into an appropriate expression vector; introducing the expression vector into an appropriate host cell; recovering the resultant transformant, obtaining an extract; and subjecting the extract to chromatography such as ion exchange, reversed phase and gel filtration, or affinity chromatography having a column to which an antibody against the fusion protein is immobilized or these columns in combination to purify the protein. Also, the addition of a polymer to e.g., an end of the protein of TPO or a derivative thereof can be carried out by, for example, mixing a polymer having a reactive group and the protein of TPO or a derivative thereof.

As the TPO or a derivative thereof modified as mentioned above, recombinant human TPO (represented also by rHuTPO or rHTPO), which is a glycosylated molecule having the same full-length amino acid sequence as that of natural TPO and polyethylene glycol (PEG) bound recombinant human megakaryocyte growth and developmental factor (PEG-rHuMGDF) (Blood 2002; 100: 3457-3469 and Semin Hematol 2000; 37: 41-49), which is a non-glycosylated molecule comprising 1-163th amino acids corresponding a bioactive domain of a natural TPO, are preferably mentioned.

In the specification, the "substance having an activity of activating c-MPL receptor" refers to a substance mediating intracellular signal transmission concerning a c-MPL receptor in the cell expressing the c-MPL receptor (more specifically, a substance activating a c-MPL receptor), and one or more (preferably three) substances inducing phosphorylation selected from (a) STAT phosphorylation in the Jak-STAT pathway, (b) MAPK phosphorylation in the Ras-MAPK pathway and (c) Akt phosphorylation in the PI3K-Akt pathway, are preferably comprised.

Whether a substance has an activity of activating c-MPL receptor or not can be checked by a known method. As the method, a method of analyzing downstream signal transmission by activation of a c-MPL receptor, is mentioned. More specifically, a method of analyzing (a) STAT phosphorylation in the Jak-STAT pathway, (b) MAPK phosphorylation in the Ras-MAPK pathway and (c) Akt phosphorylation in the PI3K-Akt pathway induced by activation of a c-MPL receptor, is mentioned. The phosphorylation can be analyzed by western blotting using a specific antibody against phosphorylated STAT, phosphorylated MAPK or phosphorylated Akt. These specific antibodies are commercially available. Note that, human c-MPL receptor whose amino acid sequence is known (see, Genbank: NP_005364) can be produced by a method such as chemical synthesis and genetic engineering technique known to those skilled in the art.

The concentration of a c-MPL receptor active substance in the medium to be used in culture of the present invention is not particularly limited as long as a mesenchymal cell is cultured in a mesenchymal cell culturing basic medium comprising a c-MPL receptor active substance in the concentration, to produce a "mesenchymal cell with promoted expression of a c-MPL receptor on the cell surface" and, for example, falls within the range of ng/mL to 10 µg/mL, preferably within the range of 2 ng/mL to 1.25 µg/mL, more preferably within the range of 20 to 125 ng/mL, further preferably within the range of 25 to 100 ng/mL and more preferably within the range of 30 to 70 ng/mL. These concentration ranges are particularly preferable if the c-MPL receptor active substance is TPO or a derivative thereof.

(Mesenchymal Cell Culturing Basic Medium)

The mesenchymal cell culturing basic medium to be used in the present invention is not particularly limited as long as a "mesenchymal cell with promoted expression of a c-MPL receptor on the cell surface" can be produced by culturing a mesenchymal cell in the medium comprising a c-MPL receptor active substance. In order to easily prepare and prevent variation per lot, a chemically synthesized medium is preferable, and one or more sugars, one or more inorganic salts, one or more amino acids, and one or more vitamins and one or more ingredients other than the aforementioned ones are preferably comprised.

Examples of the sugars can include monosaccharides such as glucose, lactose, mannose, fructose and galactose; and disaccharides such as sucrose, maltose and lactose. Of them glucose is particularly preferable. These sugars can be added alone or in combination of two or more.

Examples of the inorganic salts can include calcium chloride, calcium nitrate, copper sulfate pentahydrate, iron (III) nitrate nonahydrate, iron (II) sulfate heptahydrate, magnesium chloride hexahydrate, magnesium sulfate, potassium chloride, sodium chloride, sodium hydrogen carbonate, disodium hydrogen phosphate, disodium hydrogen phosphate dihydrate, sodium dihydrogen phosphate, sodium dihydrogen phosphate monohydrate, sodium dihydrogen phosphate dihydrate, sodium selenite pentahydrate and zinc sulfate heptahydrate. These inorganic salts can be used alone or in combination of two or more. Any one or combination of inorganic salts can be used as long as they are components advantageously functioning for producing a "mesenchymal cell with promoted expression of a c-MPL receptor on the cell surface" from mesenchymal cells.

As the amino acid(s), one or more amino acids selected from e.g., alanine, arginine, asparagine, aspartic acid, cystine, cysteine, glutamine, glycine, histidine, glutamic acid, hydroxyproline, isoleucine, leucine, lysine, methionine, phenylalanine, proline, serine, threonine, tryptophan, tyrosine and valine, and preferably L-form amino acids and those derived from the L-form amino acids such as derivatives, salts and hydrates thereof can be specifically mentioned. As arginine, for example, an arginine derivative such as L-arginine hydrochloride and L-arginine monohydrochloride can be mentioned. As aspartic acid, aspartic acid derivatives such as sodium L-aspartate monohydrate, L-aspartic acid monohydrate, potassium L-aspartate and magnesium L-aspartate can be mentioned. As cysteine, cysteine derivatives such as L-cystine dihydrochloride and L-cysteine hydrochloride monohydrate can be mentioned. As lysine, lysine derivatives such as L-lysine hydrochlorides can be mentioned. As glutamic acid, a glutamine derivative such as sodium L-glutamate can be mentioned. As asparagine, an asparagine derivative such as L-asparagine monohydrate can be mentioned. As tyrosine, tyrosine derivatives such as L-tyrosine disodium dihydrate can be mentioned. As histidine, histidine derivatives such as histidine hydrochloride and histidine hydrochloride monohydrate can be mentioned. As lysine, lysine derivatives such as L-lysine hydrochloride can be mentioned.

As the vitamins, one or more vitamins selected from e.g., biotin, choline, folic acid, inositol, niacin, pantothenic acid, pyridoxine, riboflavin, thiamine, vitamin B12, para-aminobenzoic acid (PABA), ascorbic acid, and those derived from these vitamins, such as derivatives, salts and hydrates thereof, can be specifically mentioned. For example, as choline, choline derivatives such as choline chloride can be mentioned. As niacin, niacin derivatives such as nicotinic acid, nicotinic acid amide and nicotinic alcohol, can be mentioned. As pantothenic acid, pantothenic acid derivatives such as calcium pantothenate, sodium pantothenate and panthenol, can be mentioned. As pyridoxine, pyridoxine derivatives such as pyridoxine hydrochloride, pyridoxal hydrochloride, pyridoxal phosphate and pyridoxamine, can be mentioned. As thiamine, thiamine derivatives such as thiamine hydrochloride, thiamin nitrate, bisthiamine nitrate, thiamine dicetyl sulfate, fursultiamine hydrochloride, octotiamine and benfotiamine, can be mentioned. As ascorbic acid, ascorbic acid derivatives such as ascorbic acid 2-phosphate, ascorbic acid magnesium phosphate, ascorbic acid sodium sulfate, aminopropyl ascorbyl phosphate and sodium ascorbyl phosphate, can be mentioned.

As the other components, serum such as fetal bovine serum (FBS), a buffering agent such as HEPES, an antibiotic substance such as penicillin and streptomycin, pyruvic acid, and those derived therefrom, such as derivative, salts and hydrates thereof, and phenol red can be mentioned. As a derivative of an antibiotic substance as mentioned above, sodium penicillin G, streptomycin sulfate or a penicillin-streptomycin solution can be preferably mentioned. As a pyruvic acid derivative, sodium pyruvate can be preferably mentioned. When serum is added as the other component to a mesenchymal cell culturing basic medium, the concentration of the serum within the range of 1 to 20 wt %, preferably within the range of 5 to 15 wt % and more preferably within the range of 7 to 13 wt % can be mentioned.

As specific examples of the mesenchymal cell culturing basic medium, a chemically synthesized medium known in the art, such as commercially available Dulbecco's Modified Eagle's Medium (DMEM), Iscove's Modified Dulbecco's Medium (IMDM), RPMI 1640 medium, Minimum Essential Medium (MEM), Eagle's Basal Medium (BME) and F12 medium; medium mixtures prepared by mixing two or more of these mediums in an appropriate ratio, for example, a DMEM/F12 medium (DMEM and F12 mediums are mixed in a ratio of 1:1); mediums prepared by further adding one or more substance selected from the group consisting of a serum such as FBS, an antibiotic such as penicillin and streptomycin and supplemental amino acids (preferably non-essential amino acids) to any one of these mediums, can be more preferably mentioned. In particular, a medium prepared by adding serum such as FBS, an antibiotic (preferably sodium penicillin G, streptomycin sulfate or penicillin-streptomycin solution) or a supplemental non-essential amino acid to DMEM, IMDM or RPMI 1640 medium, can be more preferably mentioned. Of them, a medium prepared by further adding serum such (preferably FBS), an antibiotic (preferably sodium penicillin G, streptomycin sulfate or a penicillin-streptomycin solution) and supplemental non-essential amino acid to DMEM, can be particularly preferably mentioned.

In the present invention, as a particularly preferable mesenchymal cell culturing basic medium, a medium prepared by adding serum (a final concentration: 10%, (preferably FBS)), a non-essential amino acid product (final concentration: 1%) and a 100 U/mL (final concentration) penicillin-streptomycin solution to a DMEM having a composition described later (hereinafter referred to as "particularly preferable basic medium of the present invention") and a medium comprising components individually in concentrations within the range of 70% to 130% relative to the components of the particularly preferable basic medium of the present invention, can be mentioned.

(Composition of DMEM)

200 mg/L anhydrous calcium chloride, 0.1 mg/L Fe$(NO_3)_3 \cdot 9H_2O$, 200 mg/L potassium chloride, 97.67 mg/L anhydrous magnesium sulfate, 6400 mg/L sodium chloride, 3700 mg/L sodium hydrogen carbonate, 125 mg/L sodium dihydrogen phosphate monohydrate, 4500 mg/L D-glucose, 15 mg/L phenol red, 110 mg/L sodium pyruvate, 84 mg/L L-arginine hydrochloride, 63 mg/L L-cystine dihydrochloride, 584 mg/L L-glutamine, 30 mg/L glycine, 42 mg/L L-histidine hydrochloride monohydrate, 105 mg/L L-isoleucine, 105 mg/L L-leucine, 146 mg/L L-lysine hydrochloride, 30 mg/L L-methionine, 66 mg/L L-phenylalanine, 42 mg/L L-serine, 95 mg/L L-threonine, 16 mg/L L-tryptophan, 104 mg/L L-tyrosine disodium salt dihydrate, 94 mg/L L-valine, 4 mg/L calcium D-pantothenate, 4 mg/L choline chloride, 4 mg/L folic acid, 7.2 mg/L i-inositol, 4 mg/L nicotinic acid amide, 4 mg/L pyridoxine hydrochloride, 0.4 mg/L riboflavin and 4 mg/L thiamine hydrochloride.

As a particularly preferable medium to be used in the culture of the present invention, a medium prepared by adding a c-MPL receptor active substance to the particularly preferable basic medium of the present invention as mentioned above can be mentioned. In particular, a medium prepared by adding a c-MPL receptor active substance alone as an active ingredient to the particularly preferable basic medium of the present invention as mentioned above can be more preferably mentioned.

To the medium to be used in culture of the present invention, e.g., LDL cholesterol, insulin, 2-(3-mercaptoethanol, an iron ion and an iron transporter may be added; however, preferably these substances are not added because differentiation induction to megakaryocytes or platelets proceeds.

(Culture Method)

The culture method in the present invention is not particularly limited as long as a "mesenchymal cell with promoted expression of a c-MPL receptor on the cell surface" can be produced by culturing the mesenchymal cell in a mesenchymal cell culturing basic medium comprising a c-MPL receptor active substance, and, for example, an adhesion culture carried out in the culture vessel coated with an extracellular matrix, can be mentioned. The culture temperature within the range of usually 12 to 45° C. and preferably 15 to 37° C. can be mentioned. The culture period within the range of 1 to 15 days, 2 to 10 days, 2 to 4 days and 3 days can be mentioned. In the culture, a mesenchymal cell may be subcultured. In subculturing, a mesenchymal cell with promoted expression of a c-MPL receptor on the cell surface is preferably selected and cultured.

(Step B)

The production method of the present invention comprises Step B after Step A. Step B is not particularly limited as long as it is a step of obtaining a mesenchymal cell with promoted expression of a c-MPL receptor on the cell surface.

In the specification, a "mesenchymal cell with promoted expression of a c-MPL receptor on the cell surface" refers to the mesenchymal cell on the surface of which a larger number of c-MPL receptors are expressed than (compared to) the number of c-MPL receptors expressed on the surface of a mesenchymal cell (hereinafter referred to as "control mesenchymal cell"), which is obtained by culturing a mesenchymal cell in the same method except that an agent for promoting expression of a c-MPL receptor is not added to a mesenchymal cell culturing basic medium; and if the mesenchymal cells constitute a cell population, refers to a cell population of mesenchymal cells in which the average number (average number per cell) of c-MPL receptors expressed on the surface of the cells (for example, cells within 10 to 100 cells comprised in the cell population) of all or part of the cell population is larger than the average number (average number per cell) of c-MPL receptors expressed on the surface of the cells (for example, cells within 10 to 100 cells comprised in the cell population) of all or part of the cell population of control mesenchymal cells. In the specification, a "mesenchymal cell with promoted expression of a c-MPL receptor on the cell surface" preferably includes a cell population of mesenchymal cells in which the ratio of c-MPL receptor positive cells is higher than that (the ratio of c-MPL receptor positive cells) in the cell population of the control mesenchymal cells. In the specification, a "mesenchymal cell with promoted expression of a c-MPL receptor on the cell surface" suitably includes a cell population of mesenchymal cells in which the ratio of the c-MPL receptor positive cells is 1% or more, preferably 2% or more and further preferably 3% or more. In the cell population of mesenchymal cells with not promoted expression of a c-MPL receptor on the cell surface, the ratio of c-MPL receptor positive cells is usually less than 0.8% (see, the ratio of c-MPL receptor positive cells in "cell population of preadipocytes (TPO−)" in Example 1 (described later)).

Whether expression of a c-MPL receptor on cell surface is promoted or not can be checked by e.g., selecting mesenchymal cells expressing a c-MPL receptor (for example, c-MPL receptor-positive mesenchymal cells) based on the presence or absence of specific binding to an antibody (preferably a labeled antibody, more preferably a fluorescence-labeled antibody) against a c-MPL receptor. As the selection method, a method of using, e.g., a cell sorter, magnetic beads or a column for adsorbing cells can be mentioned. A method of using a cell sorter can be preferably mentioned because it is a simpler and quicker method. The method of using a cell sorter is based on flow cytometry and well known to those skilled in the art.

As the "mesenchymal cell on the surface of which a larger number of c-MPL receptors are expressed than (compared to) the number of c-MPL receptors expressed on the surface of the control mesenchymal cells", the mesenchymal cell on the surface of which c-MPL receptors are expressed in the number, which is 1.5 times or more, preferably twice or more, more preferably 3 times or more and further preferably 4 times or more as large as the number of those in the control mesenchymal cells, can be preferably mentioned. As the "cell population of mesenchymal cells in which the average number (average number per cell) of c-MPL receptors expressed on the surface of the cells of all or part of the cell population is larger than the average number (average number per cell) of c-MPL receptors expressed on the surface of the cells of all or part of the cell population of control mesenchymal cells", a cell population of the mesenchymal cells in which the average number (average number per cell) of c-MPL receptors expressed on the surface of the cells of all or part of the cell population is 1.5 times or more, preferably twice or more, more preferably 3 times or more and further preferably 4 time or more as large as that in the control mesenchymal cells, can be preferably mentioned.

As the method for obtaining a "mesenchymal cell with promoted expression of a c-MPL receptor on the cell surface", a method of directly obtaining a cell population obtained by culturing in Step A, more specifically a cell population comprising a "mesenchymal cell with promoted expression of a c-MPL receptor on the cell surface", may be employed; or a method of selecting a "mesenchymal cell with promoted expression of a c-MPL receptor on the cell surface" from the cell population obtained by culturing in Step A, may be employed. In the specification, selecting a predetermined mesenchymal cell includes (p) isolating a predetermined mesenchymal cell alone from a cell population and (q) applying a treatment such that the ratio (ratio of cells in number) of the predetermined mesenchymal cell comprised in the cell population after selection is further increased compared to the ratio (ratio of cells in number) of the predetermined mesenchymal cell comprised in the cell population before selection, for convenience sake.

A method for selecting a "mesenchymal cell with promoted expression of a c-MPL receptor on the cell surface" is not particularly limited; however, in order to more simply and quickly select a desired mesenchymal cell, a method for selecting a mesenchymal cell with promoted expression of a c-MPL receptor on the cell surface based on the presence or absence of specific binding to an antibody (preferably a labeled antibody, more preferably a fluorescence-labeled antibody) against a c-MPL receptor, can be mentioned. As the method of selecting a mesenchymal cell, a method of using e.g., a cell sorter, magnetic beads or column for adsorbing cells as mentioned above, can be mentioned. A method using a cell sorter is preferably mentioned because it is simpler and quicker method.

<Method for Promoting Expression of a c-MPL Receptor on the Surface of a Mesenchymal Cell>

The method for promoting expression of a c-MPL receptor on the surface of a mesenchymal cell according to the present invention (hereinafter simply referred to as "the promoting method of the present invention") is not particularly limited as long as it comprises Step A of culturing the mesenchymal cell in a mesenchymal cell culturing basic medium comprising a c-MPL receptor active substance. Such step A is the same as Step A of the production method of the present invention.

<Agent for Promoting Expression of a c-MPL Receptor on the Surface of a Mesenchymal Cell>

The agent for promoting expression of a c-MPL receptor on the surface of a mesenchymal cell according to the present invention (hereinafter simply referred to as "the expression promoting agent of the present invention") is not particularly limited, as long as it comprises a c-MPL receptor active substance, and preferably comprises the c-MPL receptor active substance as an active ingredient, and more preferably comprises the c-MPL receptor active substance as a single active ingredient.

The expression promoting agent of the present invention may consist of a c-MPL receptor active substance alone or a preparation of c-MPL receptor active substance obtained by a conventional method. The dosage form of the expression promoting agent of the present invention may be a solid preparation such as a powder and granule or a liquid preparation such as a solution, an emulsion and a suspension. When a c-MPL receptor active substance is formed into a preparation, if necessary in forming a preparation, an appropriate pharmaceutically acceptable carrier such as an excipient, a binder, a solvent, a solubilizing agent, a suspending agent, an emulsifying agent, an isotonic agent, a buffering agent, a stabilizing agent, a soothing agent, a preservative, an antioxidant, a coloring agent, a lubricant, a disintegrant, a wetting agent, an adsorbent, a sweetening agent and a diluent can be blended as an optional component.

The expression promoting agent of the present invention can be used by adding it to a mesenchymal cell culturing basic medium, followed by culturing the mesenchymal cell in vitro in the medium. As the concentration of the expression promoting agent to be added to the basic medium, the range of 1 ng/mL to 2.5 µg/mL, preferably the range of 5 ng/mL to 500 ng/mL in terms of a concentration of the dry-state c-MPL receptor active substance equivalent concentration can be mentioned. Such concentration range is particularly preferably mentioned if the c-MPL receptor active substance is TPO.

The present invention will be more specifically described by way of Examples below; however, the present invention is not limited to these Examples. Note that, the concentrations of components of a medium described in the following Examples represent final concentrations in the medium.

Example 1

[Culturing the Mesenchymal Cell in a Mesenchymal Cell Culturing Basic Medium Comprising a c-MPL Receptor Active Substance]

In order to check whether expression of a c-MPL receptor on a cell surface of a mesenchymal cell is promoted or not, the following culture experiment was carried out by culturing mesenchymal cells in a mesenchymal cell culturing basic medium comprising a c-MPL receptor active substance. Note that, in the culture experiment, preadipocytes were used as the mesenchymal cells.

Figure 1:
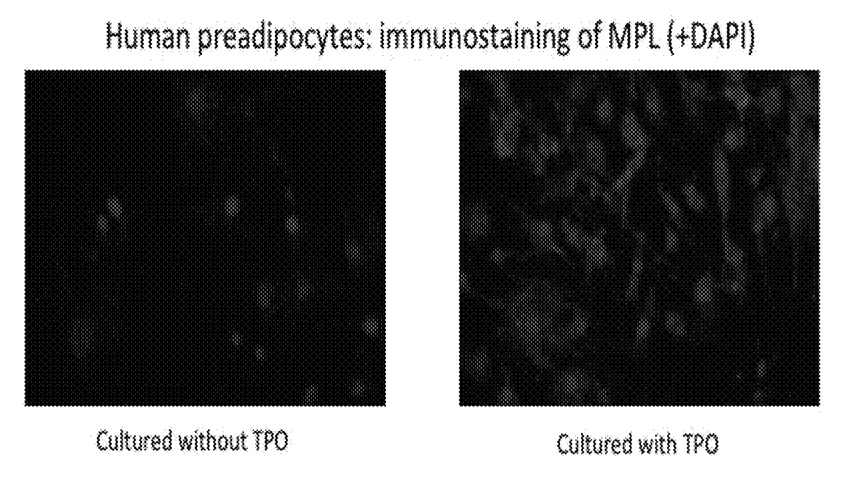
FIG. 1 shows the observation results of fluorescence after human preadipocytes are cultured for three days and immuno-stained with "fluorescence-labeled anti c-MPL antibody" and "DAPI". The right panel shows the results of human preadipocytes cultured in a culture medium prepared by adding TPO; whereas the left panel shows the results of human preadipocytes cultured in a culture medium prepared by not adding TPO.

Human primary culture preadipocytes (Human Preadipocytes: HPAd) manufactured by CELL APPLICATIONS were prepared. A culture dish was coated with collagen and then a culture medium was added to the dish. As the culture medium, DMEM medium (Dulbecco's Modified Eagle's Medium, manufactured by Life Technology Co.), to which a 10% fetal bovine serum (manufactured by Sigma), a 1% non-essential amino acid(s) (manufactured by Life Technology Co.), a 100 U/mL penicillin-streptomycin solution (manufactured by Life Technology Co.) and 50 ng/mL recombinant human TPO (manufactured by R&D Systems) were added, was used. The preadipocytes were cultured in the culture medium at 37° C. for 3 days. After culture, the preadipocytes were separately taken. The preadipocytes (hereinafter referred to as "the cell population of preadipocytes (TPO+)") were labeled with a fluorescence-labeled anti c-MPL antibody (manufactured by BD Bioscience), and fluorescence was measured by flow cytometry. When the ratio of c-MPL receptor positive cells was determined in this manner, the ratio was 3.68±0.39%. Note that, the cell population of preadipocytes (TPO+) was immuno-stained with a "fluorescence-labeled anti c-MPL antibody" and "DAPI (4',6-diamidino-2-phenylindole)". The results are shown in FIG. 1, the right panel. In the right panel, cells emitting fluorescence derived from the fluorescence-labeled anti c-MPL antibody are observed around the circular fluorescence emitted from nuclei stained with DAPI. In short, a large number of the cells, i.e., c-MPL receptor positive cells are present.

In contrast, the preadipocytes (hereinafter referred to as "cell population of preadipocytes (TPO−)") were cultured in the same method except that recombinant human TPO was not added to a culture medium. When the ratio of the c-MPL receptor positive cells was determined by flow cytometry, the ratio was 0.67±0.12%. Note that, the cell population of preadipocytes (TPO−) was immuno-stained with a "fluorescence-labeled anti c-MPL antibody" and "DAPI". The results are shown in FIG. 1, the left panel. In the left panel, cells emitting fluorescence derived from the fluorescence-labeled anti c-MPL antibody are observed around the circular fluorescence emitted from nuclei stained with DAPI. In short, a smaller number of the cells, i.e., c-MPL receptor positive cells, are present.

As mentioned above, it was demonstrated that if TPO is added to a culture medium for culturing preadipocytes, the ratio of the c-MPL receptor positive cells is increased about 5.5 time as large as the ratio of the case where TPO is not added.

Example 2

[Differentiation Induction of Preadipocytes into Megakaryocyte/Platelets]

In order to check whether "cell population of preadipocytes (TPO+)" obtained in Example 1 can be actually used for efficient production of megakaryocytes/platelets (megakaryocyte and/or platelet), differentiation of preadipocytes into megakaryocyte/platelets was induced in accordance with the method described in Patent Document 1.

A culture dish was coated with collagen and then a culture medium was added to the dish. As the culture medium, MKLI medium (megakaryocyte lineage induction medium)

known as a medium which can induce differentiation of hematopoietic stem cells into megakaryocytes/platelets, was used. The MKLI medium was prepared by adding 2 mM L-glutamine (manufactured by Life Technology), a 100 U/mL penicillin-streptomycin solution (manufactured by Life Technology), 0.5% BSA (manufactured by Sigma), 4 µg/mL LDL cholesterol (manufactured by Sigma), 200 µg/mL iron-saturated transferrin (manufactured by Sigma), 10 µg/mL insulin (manufactured by Sigma), 50 µM 2-β-mercaptoethanol (manufactured by Life Technology), nucleotides (ATP, UTP, GTP, and CTP, 20 µM for each) (manufactured by Life Technology) and 50 ng/mL human thrombopoietin (TPO, manufactured by Stem Cell Technologies) to IMDM medium (Iscove's Modified Dulbecco's Medium, manufactured by Life Technology).

The "cell population of preadipocytes (TPO+)" obtained in Example 1 was cultured in MKLI medium as mentioned above at 37° C. and in the conditions of a $CO_2$ concentration of 5% for 7 days. After culture, the cell population was separately taken and the ratio (%) of CD41 (specific marker of megakaryocytes or platelets) positive cells in the cell population was determined. Such determination was carried out by directly labeling with FITC (fluorescein isothiocyanate)-labeled anti CD41 antibody and using flow cytometry. The ratio of the CD41 positive cells in the cell population was 28.5±2.1%.

In contrast, the ratio of CD41 positive cells in the "cell population of preadipocytes (TPO−)" obtained in Example 1 was determined by flow cytometry. The ratio was 17.0±5.7%.

As mentioned above, it was demonstrated that the number of megakaryocytes/platelets produced from the preadipocytes ("cell population of preadipocytes (TPO+)") obtained from culture in a medium comprising recombinant TPO is about 1.7 times as large as that produced from preadipocytes ("cell population of preadipocytes (TPO−)") obtained from culture in a medium not comprising recombinant TPO.

INDUSTRIAL APPLICABILITY

According to the present invention, expression of c-MPL on the surface of a mesenchymal cell can be simply and efficiently promoted. More specifically, according to the present invention, a mesenchymal cell with promoted expression of a c-MPL receptor on the cell surface can be simply and efficiently produced.

The invention claimed is:

1. A method for producing a mesenchymal cell with promoted expression of a c-MPL receptor on a cell surface, comprising:
   Step A of culturing the mesenchymal cell in a culture medium for culturing a mesenchymal cell comprising a MPL proto-oncogene, thrombopoietin receptor (c-MPL) receptor active substance but not comprising LDL cholesterol, insulin, 2-β-mercaptoethanol, an iron ion and an iron transporter; and
   Step B of obtaining the mesenchymal cell with promoted expression of a c-MPL receptor on the cell surface, and wherein said mesenchymal cell is a preadipocyte.

2. The method for producing a mesenchymal cell with promoted expression of a c-MPL receptor on a cell surface according to claim 1, wherein the c-MPL receptor active substance is one or more substances selected from the group consisting of thrombopoietin (TPO), a derivative thereof, Romiplostim and Eltrombopag olamine.

3. The method for producing a mesenchymal cell with promoted expression of a c-MPL receptor on a cell surface according to claim 1, wherein a ratio of c-MPL receptor-positive mesenchymal cells in the mesenchymal cell population obtained in Step B is 1% or more.

4. A method for promoting expression of a c-MPL receptor on a surface of a mesenchymal cell, comprising Step A of culturing the mesenchymal cell in a culture medium for culturing a mesenchymal cell comprising a c-MPL receptor active substance but not comprising LDL cholesterol, insulin, 2-β-mercaptoethanol, an iron ion and an iron transporter
    and wherein said mesenchymal cell is a mesenchymal stem cell or a preadipocyte.

5. The method for producing a mesenchymal cell with promoted expression of a c-MPL receptor on a cell surface according to claim 2, wherein a ratio of c-MPL receptor-positive mesenchymal cells in the mesenchymal cell population obtained in Step B is 1% or more.

6. The method for promoting expression of a c-MPL receptor on a surface of a mesenchymal cell according to claim 4, wherein the c-MPL receptor active substance is one or more substances selected from the group consisting of TPO, a derivative thereof, Romiplostim and Eltrombopag olamine.

\* \* \* \* \*

UNITED STATES PATENT AND TRADEMARK OFFICE
CERTIFICATE OF CORRECTION

PATENT NO.         : 10,704,024 B2
APPLICATION NO.    : 15/753028
DATED              : July 7, 2020
INVENTOR(S)        : Yumiko Matsubara et al.

Page 1 of 1

It is certified that error appears in the above-identified patent and that said Letters Patent is hereby corrected as shown below:

In the Claims

At Column 25, Claim number 4, Line number 7:
--and wherein said mesenchymal cell is a mesenchymal stem cell or preadipocyte--
Should read:
--and wherein said mesenchymal cell is a preadipocyte--

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*